(12) United States Patent
Hayun et al.

(10) Patent No.: US 9,588,233 B2
(45) Date of Patent: Mar. 7, 2017

(54) X-RAY RADIATION DETECTOR WITH AUTOMATIC EXPOSURE CONTROL

(71) Applicant: CMT MEDICAL TECHNOLOGIES LTD., Yokneam Ilit (IL)

(72) Inventors: Ami Ben Hayun, Ramat Yishay (IL); Alex Shtengel, Yoqneam (IL); Guy Hevel, Zichron Yakov (IL)

(73) Assignee: CMT MEDICAL TECHNOLOGIES LTD, Yokneam Ilit (IL)

( * ) Notice: Subject to any disclaimer, the term of this patent is extended or adjusted under 35 U.S.C. 154(b) by 0 days.

(21) Appl. No.: 14/944,931

(22) Filed: Nov. 18, 2015

(65) Prior Publication Data

US 2016/0070003 A1 Mar. 10, 2016

Related U.S. Application Data

(62) Division of application No. 13/471,970, filed on May 15, 2012, now Pat. No. 9,201,149.

(60) Provisional application No. 61/468,408, filed on Mar. 28, 2011.

(51) Int. Cl.
| | |
|---|---|
| *G01T 1/20* | (2006.01) |
| *A61B 6/00* | (2006.01) |
| *H05G 1/42* | (2006.01) |
| *G01T 1/02* | (2006.01) |

(52) U.S. Cl.
CPC ............ *G01T 1/2006* (2013.01); *A61B 6/542* (2013.01); *G01T 1/2018* (2013.01); *G01T 1/023* (2013.01); *H05G 1/42* (2013.01)

(58) Field of Classification Search
CPC ............. A61B 6/542; H05G 1/42; H05G 1/44
See application file for complete search history.

(56) References Cited

U.S. PATENT DOCUMENTS

| 6,404,854 B1 * | 6/2002 | Carroll | .................. A61B 6/145 |
| | | | 348/E3.02 |
| 7,606,347 B2 * | 10/2009 | Tkaczyk | ................ A61B 6/032 |
| | | | 378/19 |

OTHER PUBLICATIONS

"Real-Time Denoising of Medical X-ray Image Sequences: Three Entirely Different Approaches" ICIAR 2006, LNCS 4142, pp. 479-490, 2006 to Hensel et al.*
"A wafer-scale CMOS APS imager for medical X-ray applications", presented at Image Sensors Europe (2010), available at http://www.teledynedalsa.com/public/corp/pdfs/papers/DALSA_IISW2009_CMOS_Medical.pdf to Korthout et al.*

* cited by examiner

*Primary Examiner* — David J Makiya
*Assistant Examiner* — Kenneth J Malkowski
(74) *Attorney, Agent, or Firm* — William Dippert; Laurence Greenberg; Werner Stemer

(57) ABSTRACT

A radiation detection system comprises a scintillator for converting radiation to visible light; two buttable CMOS wafers; an adjacent acquisition board, for acquiring pixel values; and a processing board for detecting image edge is described. The butt of each adjacent CMOS wafers pair is made such that the total width of two peripheral pixel lines and the spacing between them sums to a whole number of pixel pitch.

4 Claims, 6 Drawing Sheets

X-RAY RADIATION DETECTOR WITH AUTOMATIC EXPOSURE CONTROL

CROSS REFERENCE TO RELATED PATENT APPLICATIONS

This application is a divisional of co-pending U.S. patent application Ser. No. 13/471,970 entitled "X-Ray Radiation Detector", which is in turn based upon and claims the priority of U.S. Provisional Patent Application No. 61/486,408, filed May 16, 2011, entitled "A Radiation Detector", each of which is incorporated herein by reference in its entirety.

FIELD OF THE INVENTION

The current invention relates to a solid state X-ray Flat Panel radiation Detector (FPD) for medical application, and more specifically to an X-ray detector integrated with Automatic Exposure Control, image correction, and defective pixel compensation.

BACKGROUND OF THE INVENTION

Flat Panel radiation Detectors (FPDs) are the current standard in static and dynamic radiography clinical applications. Static applications include cranial, skeletal, podiatric, thoracic, and lung exposures. Dynamic (Fluoroscopy) clinical applications include gastrointestinal tract, urogenital tract, lymphography, endoscopy, myelography, venography, digital angiography, and digital subtraction angiography.

Further, FPDs quickly penetrate new clinical fields such as dental imaging, minimal invasive surgery, and mammography. Further, they are widely used in non-medical application such as non-distractive testing's (NDT) and security screening.

All radiological systems, both medical and industrial, consist of a radiation source (High Voltage (HV) generator and X-ray tube), and of a radiation detector, such as FPD. The imaged object is positioned between the radiation source and the detector. The object absorbs part of the X-ray radiation. The detector's signal is responsive to the unabsorbed radiation, and is sent to a viewing station for further processing and display.

In an X-ray system, control of the scan operation is a combined task of the generator and the FPD, and it consists of mutual sending of pulses between them, pulses that are designated "prep request" and "X-ray enable". The operation is initiated by the human operator who presses a button (or a pedal), which triggers the X-ray generator to start a preparation phase. The generator then sends a "prep-request" pulse to the FPD and waits for an "X-ray enable" response of the FPD before starting the actual radiation. Upon sending the "X-ray enable" pulse, the FPD starts acquiring the signal.

The FPD acquisition time is set to be always larger than the expected X-ray pulse: In a case of dynamic X-ray system, where the scan consists of a long sequence of low-dose X-ray pulses, the FPD acquisition timing consists of train of acquisition pulses, each such acquisition pulse is synchronized with a corresponding X-ray pulse, and each is longer than the corresponding X-ray pulse.

In static X-ray systems, the acquisition period is controlled by Automatic Exposure Control (AEC) sub-system. The AEC sub-system used in the art typically uses of up to five small radiation-detection panels mounted between the patient and front of the FPD. The AEC outputs signals, each proportional to the radiation impinging on one of said small radiation-detection panels, are used for controlling the High voltage generator powering the X-Ray tube. The generator is instructed by the user to select one or more of said AEC outputs signals and to apply predefined function on them for obtaining a single value.

For example, in chest radiography, the generator uses signal of the two upper AEC small radiation-detection panels, averages them, and uses the average as the single value. Said single value is integrated, and when the integral crosses a predefined threshold value, the HV generator stops, and the X-ray tube stops producing radiation. Therefore, the AEC sub-system is being operated in "slave" mode only, where the generator collects its signal and performs the required processing for obtaining a single time-increasing value, for comparing it to a preset threshold and stopping the radiation once the threshold value is reached. One reason for this setup is that the AEC sub-system is built as separate unit, mounted in front of the FPD. Thus, any further electronics or electronic board will block the beam and interfere with the proper FPD operation.

Focusing again on the FPD, it consists of as many as millions pixels, the resulting signal of each of the pixels is a function of the radiation flux on that pixel. Said function depends on the physical characteristics of the individual pixel, which are: the sensitivity, defined as the radiation-to-electrical energies conversion factor, the dark signal, and inherent non-linearity. Consequently, for obtaining proper image of the scanned object, the image has to be compensated for the variation in physical characteristics of each pixel.

Typically, a set of three corrections is utilized for each acquired image, either static or dynamic: Offset (dark signal) removal, Gain correction and Defective-pixels replacement. Dark signal is taken close to the clinical scan: either closely before, or right after, and the resulting matrix is kept on the FPD memory or in the host system. Gain correction factors are evaluated by taking a uniform (no object) image and assigning correction factor for each of the pixel which inversely proportional to its measured value.

For the defective pixels, FPD systems typically use a defective-pixel correction mean, consisting of an algorithm for detecting these defective pixels. Said algorithm consists of testing the above described physical characteristics and listing the pixels with exceptional characteristics, exceeding pre-set thresholds. Further, said defective-pixel correction mean consists of an algorithm for actually correcting the image values associated with the defective pixels. Typically, said algorithm consists of replacing the data of the defective pixels by some average of neighboring-pixels data. These three corrections consist of storing large correction matrices and operating corrections in real-time. Therefore, the correction operations are done in the host systems, not in the FPD.

FPDs are built to fit into slim geometries. For example, FPDs are being inserted in film-cassette and Compute Radiography (CR) Buckys, for upgrading analog or CR rooms into digital ones.

Many prior inventions describe modifications of the above-described calibration scheme:

JP2000126162 discloses a radiographic image processing system that outputs two images: One with corrected pixel defects and one with uncorrected pixel defects.

JP2000132662 discloses a radiographic image processing system that gives a warning when the number of defective pixels exceeds a given value, and provides information related to the defect.

JP2008229102 discloses system which enables radiographic imaging to be continued for a while after occurrence of pixel defects that may lower image quality and minimizes adverse effects of the pixel defects.

U.S. Pat. No. 7,203,279 discloses radiographic mode designator which designates a non-standard radiographic mode and a signal corrector which uses defect information stored in one of non-standard image defect information memories for correcting X-ray detection signals outputted from the FPD, thus, making it unnecessary to collect output signals for pixel defect information acquisition from the FPD all over again.

JP2009201586 discloses radiographic apparatus capable of executing appropriate afterimage correction of a radiation image according to the state of an afterimage based on the charge accumulation time in a FPD at each pixel position.

JP2009219691 discloses radiographic apparatus which is correctly discriminating whether an image defect on a detected radiation image is an image defect due to dust or an image defect due to the defective pixel of an FPD, provides a defect discriminating method according to whether the pixel is defective both in dark image and flat (no object) image or only in the flat image.

However, all the above referenced inventions assume that at least part of the correction scheme is made in the host system. This implies installing specialized boards and/or software in the host system, thus making installation of the system host-dependent, and obstructs the upgrading of existing X-ray rooms.

With respect to the AEC sub-system:

U.S. Pat. No. 5,617,462 discloses AEC mechanism, e.g., CCD camera, which provides outputs for a microprocessor for analyzing them and for adjusting the X-ray technique rapidly, thus reducing exposure time of X-rays.

U.S. Pat. No. 6,233,310 discloses AEC system which combines a patient model with a closed loop brightness control, using a parameter that does not affect image quality.

U.S. Pat. No. 7,194,065 discloses AEC which compensates for the varying of distances: The distance from the X-ray source and the patient and the distance from the X-ray source and the AEC.

Clearly, all the above inventions assume that the AEC is mounted in front of the FPD or adjacent to it. Therefore, the AECs consist of panels for dose measurements that are virtually almost transparent to the radiation. The rest of the AEC circuitry, which includes preamplifiers, processing electronic and memory boards, is located elsewhere. This fact has no drawback when referring to a stand-alone system where the FPD, AEC and the accompanying preamplifiers, electronic boards and cablings are all enclosed in Bucky mean, which is also provided by the same manufacturer. However, if installed in existing system, the described AEC systems require additional space, which might be scarce in various systems, for example, in portable FPD, in mobile systems and in upgrading of existing film- or CR-systems.

SUMMARY OF THE INVENTION

It is an aspect of the present invention to perform corrections of defective pixels, which is conformal with the edge-information of the image.

It is another aspect of the current invention to provide a radiation detector comprising: primary, anterior detection array; and a secondary, posterior detection array, wherein said primary detection array consists of a scintillator, optically coupled to CMOS active pixel sensor array (APS array), and said secondary array consists of a scintillator and array of imaging sensors.

In some embodiments, a radiation detection system comprising: a scintillator capable of converting the radiation to visible light; at least two buttable CMOS wafers; an adjacent acquisition board, for acquiring pixel values; and at least one processing board capable of image edge detection, wherein the butt of each pair of adjacent CMOS wafers is made such that the total width of the two peripheral pixel lines and the spacing between them sums to a whole number of pixel pitch, N, and wherein said processing board:

a) subtracts the corresponding data of an offset table from pixel values;

b) multiplies the resulted value by the data of the skewed gain table;

c) substitutes the values of at least one defective pixel by a value derived from values of pixels in a zone around said at least one defective pixel, in a way that the image edge is not affected; and d) produces N virtual data lines with information derived from the two peripheral lines and the lines adjacent to them, wherein said data is composed such that edges presented in the peripheral and adjacent lines is conserved in the additional N lines.

In other embodiments, the total width of the two peripheral pixel lines and the spacing between them sums to a single pixel pitch.

In yet other embodiments, the total width of the two peripheral pixel lines and the spacing between them sums to double the pixel pitch.

It yet another embodiment, substituting a values of a defected pixel by a value derived from values of pixels in a zone around said defective pixel, in a way that the image edge is not affected comprises interpolating values of pixels located on one side of the detected image edge passing through said defective pixel.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Unless marked as background or art, any information disclosed herein may be viewed as being part of the current invention or its embodiments.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE INVENTION

Figure 1:
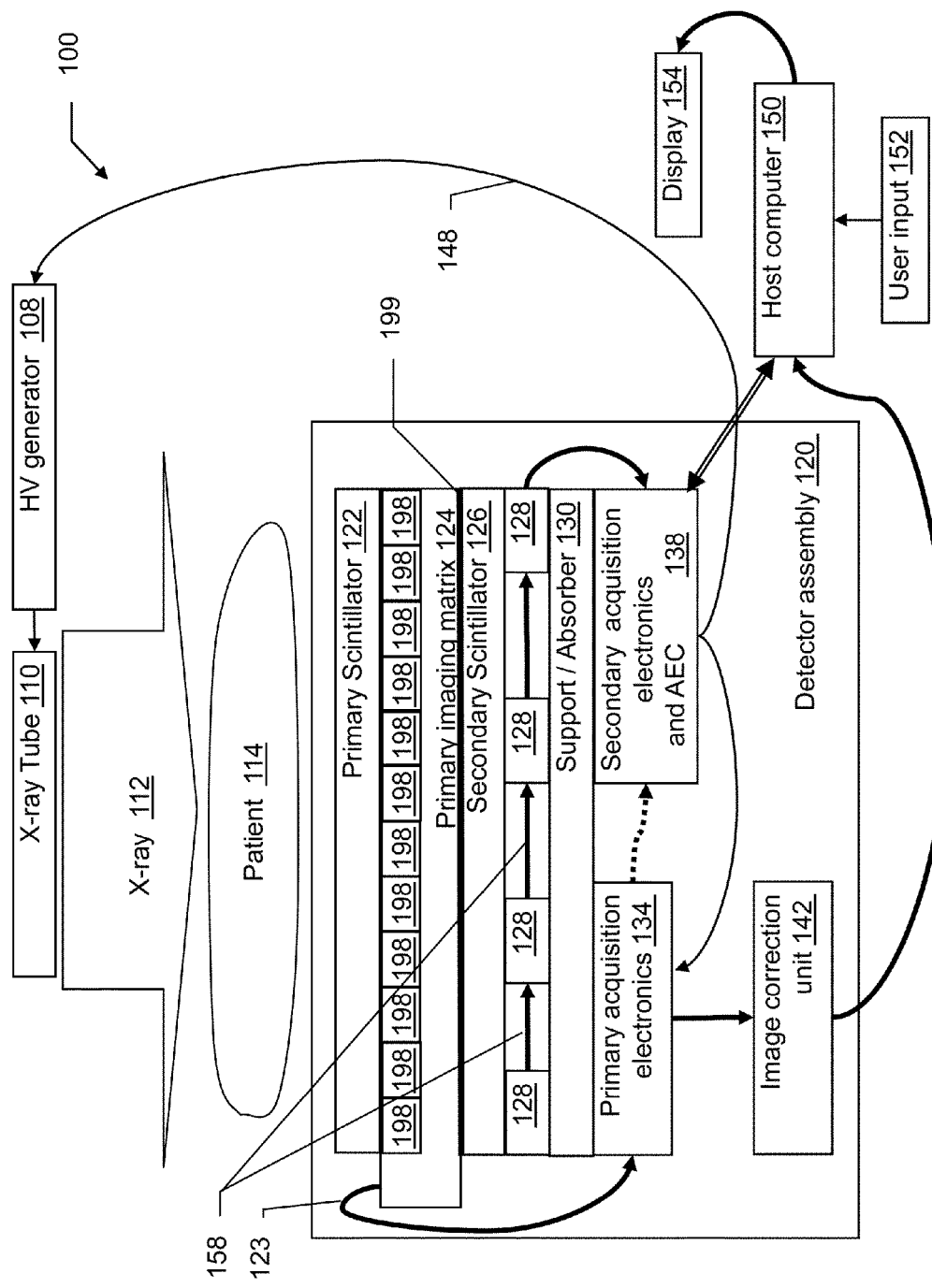
FIG. 1 schematically depicts an exemplary design of the mechanical layout of one aspect of the invention, showing the primary and secondary radiation detectors according to the current invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts. The drawings are generally not to scale. For clarity, non-essential elements were omitted from some of the drawings.

To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like.

It should be understood that the various embodiments are not limited to the arrangements and instrumentality shown in the drawings.

FIG. 1 depicts schematic drawing of an exemplary embodiment of the invention.

X-Ray imaging system 100 comprises a host computer 150 such as a Personal Computer (PC) connected to user input devices 152 such as keyboard and mouse and a display 154. System 100 further comprise a High Voltage (HV) generator 108, supplying HV to an X-ray tube 110. X-ray radiation 112, generated by X-ray tube 110 passes through the imaged patient 114 and impinges on the detector assembly 120.

Preferably, radiation detector assembly 120 is sized to fit into slim geometries. For example, to be inserted in film-cassette and Compute Radiography (CR) Buckys, for upgrading analog or CR rooms into digital ones.

Heavy arrows in the FIG. 1 indicate data flow, while thin arrow indicates flow of commands. However, it should be noted that some commands and data channels that are not essential to the explanation of the main features of the invention may have been omitted in this schematic representation.

The radiation detector within detector assembly 120 comprises of two subsequent detection arrays: a primary detector array, frontal to the radiation, and a secondary detector array, behind the primary detector array.

The primary detector array consists of scintillator-imaging array design. The primary scintillator 122 converts the impinging X-ray radiation into visible light. The primary imaging matrix 124 (also termed as primary acquisition electronics 124) of the primary detector array comprises an array of pixels, each converting the visible light into electrical signal.

In one optional embodiment of the invention, the primary scintillator 122 is column-grown Cesium Iodide (CsI) doped with Thallium (Tl). X-ray photons that hits the CsI(Tl) typically transfers its energy to the electrons of the Cesium or the Iodine. Part of the energy (about 5%) is transmitted to the Thallium, elevating it into excited state. Upon returning to the ground state, the Thallium emits green (565 nm) photon. Said photon may be emitted to any direction, but the columnar shape of the host CsI layer acts as light guide to the photon and directs it to the layer face, either to the top or the bottom of the layer. Typically, a thin reflective coating layer is deposited on the topside (facing the patient 114) of the scintillator (not shown in this figure), to further collect the up-guided light photons.

The primary imaging matrix 124 of the primary array consists of a matrix of CMOS Active Pixel Sensors (APS). The primary imaging matrix 124 is optically coupled to the lower face of primary scintillator 122. Each such APS converts the flux of visible light (green or blue light in the case of CsI(Tl)) into electrical current that charges internal capacitor. The Voltage on the capacitor is then sent to further amplification, processing and digitization.

In typical clinical application, the CsI(Tl) absorbs about 90% of the impinging radiation energy. The residual 10% crosses the CsI(Tl) layer, as well as the CMOS (and substrate) layer of primary imaging matrix 124. Further, characteristic fluorescent radiation of the Cesium (with energy in the 30-35 kV range) and the Iodine (28-33 kV) is emitted from the primary scintillator 122 and adds to the residual unabsorbed radiation. It should be noted that scintillator materials other than CsI(Tl), and sensors arrays other than CMOS APS may be used for primary scintillator 122 and primary imaging matrix respectively within the general scope of the current invention.

It is an aspect of the invention that a secondary scintillator 126 is mounted below said primary imaging matrix 124, which absorbs the residual radiation and some of the fluorescence radiation, and converts it to visible light. Said secondary scintillator 126 may also be CsI(Tl), which absorbs the characteristic radiation efficiently. However, for the purpose of cost-reduction and for increased light output, said CsI(Tl) layer might not be column-grown. Other materials may be used in embodiments of the invention. For example, Gadolinium-OxySulfide (GOS) doped with Terbium (Tb) or Praseodymium (Pr). GOS samples are available in powder form, glued on cardboard-like substrate. See, for example, in the DRZ® family of Kyokko (Mitsubishi Chemical).

A secondary matrix array of light sensors 128 is mounted, and optically coupled below said secondary scintillator 126. In one embodiment of the invention said secondary array is CMOS APS matrix. In another embodiment said array is an array of discrete light sensitive photodiodes. For example, array of Silicone photodiodes with preamp can be used such as Hamamatsu's S9269 or S9270. Alternatively, photodiodes without preamp may be used, such as, for example, Hamamatsu's S8650. Alternatively yet, each diode may consist of an array of smaller photodiodes, as, for example, Hamamatsu's S8558 diode array.

It should be noted that both X-ray detectors are kept in light-tight to avoid stray light from arriving at the light sensitive sensors. Optionally, a light-opaque layer 199 is placed between the two detection devices (primary and secondary), for avoiding cross illumination. In some embodiments, a thin, light absorbing but X-ray transparent layer is used.

In some embodiments, the secondary detector is constructed such that secondary scintillator 126 is away from the incoming X-ray radiation in relation to sensors 128. That is, sensors 128 are adjacent to the primary imaging matrix 124, while secondary scintillator 126 is between sensors 128 and support 130. In this case, a thin light absorbing layer 199 may be placed between the substrate of the primary imaging matrix 124 and the substrate of the array of secondary sensors 128. Optionally, one of these substrates is constructed to be light absorbing to perform the function of preventing light from one scintillator to illuminate the sensors of the other sensor array. In an embodiment, the same light-opaque substrate is used for supporting the primary imaging sensors 198 on one side and the secondary sensors on its other side.

It should be noted that sensors 128 in the secondary matrix array of light sensors need not cover the entire imaging area of primary scintillator 122. Instead, sensors 128 may be scattered to enable sampling of the X-ray radiation flux in a plurality of locations. Similarly, secondary scintillator 126 may cover the locations of sensors 128 instead of the entire area of the primary scintillator 122. Additionally, pixels (or individual sensors) size of secondary matrix array may be significantly larger than pixels in the primary imaging sensors 198 of the primary imaging matrix 124. For example, pixels of the second array may be as large as 5 mm$^2$, while typical pixel size of the primary array is 0.15 mm$^2$.

The entire X-ray detection section of detector assembly 120 is optionally mechanically supported by support 130. Optional support 130 is preferably made of X-ray absorbing material to protect the electronics within detector assembly 120 from X-ray radiation.

In an the exemplary embodiment depicted in FIG. 1, a plurality of electric wires 123 bonded to said CMOS APS layer (imaging matrix of primary array 124) on one side, are connected to the primary acquisition electronics 134 located behind a protective layer of Support 130. Said protective layer might be, for example, a 2 mm Tantalum sheet or similar high-z material. Primary acquisition electronic 134 contains electronics for muxing and arranging the data. Further it may contain the sub-circuit shown in FIG. 4, which is described below. Further, said primary acquisition electronics 134 is optionally connected to the secondary acquisition electronics 138. Therefore, said secondary electronics 138 board may use signals of the primary detector as input, either signal that are already processed and digitized by the primary CMOS APS or by the primary acquisition electronics 134, or raw data from the primary imaging matrix 124, which said secondary acquisition electronics 138 may processes and uses as inputs.

Signals from the secondary detector array 128 may be used by an AEC function within the secondary acquisition electronics 138, for performing Automatic Exposure Control (AEC) functions such as stopping the production of X-ray radiation by X-ray tube 110 by turning off HV from HV generator 108 using command line 148. AEC function may further control other functions of detector assembly 120 and/or system 100 such as initiation of X-ray exposure by controlling HV generator 108, starting and terminating data acquisition of the primary imaging matrix 124 by controlling the primary acquisition electronics 134, and starting and terminating data acquisition of the secondary array of sensors 128 by controlling the secondary acquisition electronics 138.

In some embodiments, a signal from the host computer initiates the "arming", or activation of the AEC function in a monitoring mode. Alternatively, "armed" mode is the default mode. In armed mode, the AEC function monitors the level of X-Ray radiation on the detector assembly 120 by monitoring the signal levels on secondary sensors 128 and/or on selected number of pixels of the primary imaging matrix. This monitoring is done at high sampling rate, while data is not acquired or stored for imaging purposes. Once X-Ray level indicates that an X-ray source was activated, for example by a direct signal from host comport 150 or other means, AEC function activates data acquisition mode of the primary acquisition electronics 134. Additionally, the AEC function optionally begins monitoring the accumulated X-ray exposure in order to determine when sufficient X-ray radiation arrived at the detector assembly 120 and command one or both of the following actions: terminate the X-ray production; and/or terminate data acquisition of primary acquisition electronics 124. These actions prevent over exposure of the X-ray image, yet ensure sufficient exposure. It should be noted that X-ray production is preferably terminated after a preset time for patient safety and for operating with detectors not equipped with AEC functions, or for operation without AEC functions.

Figure 2:
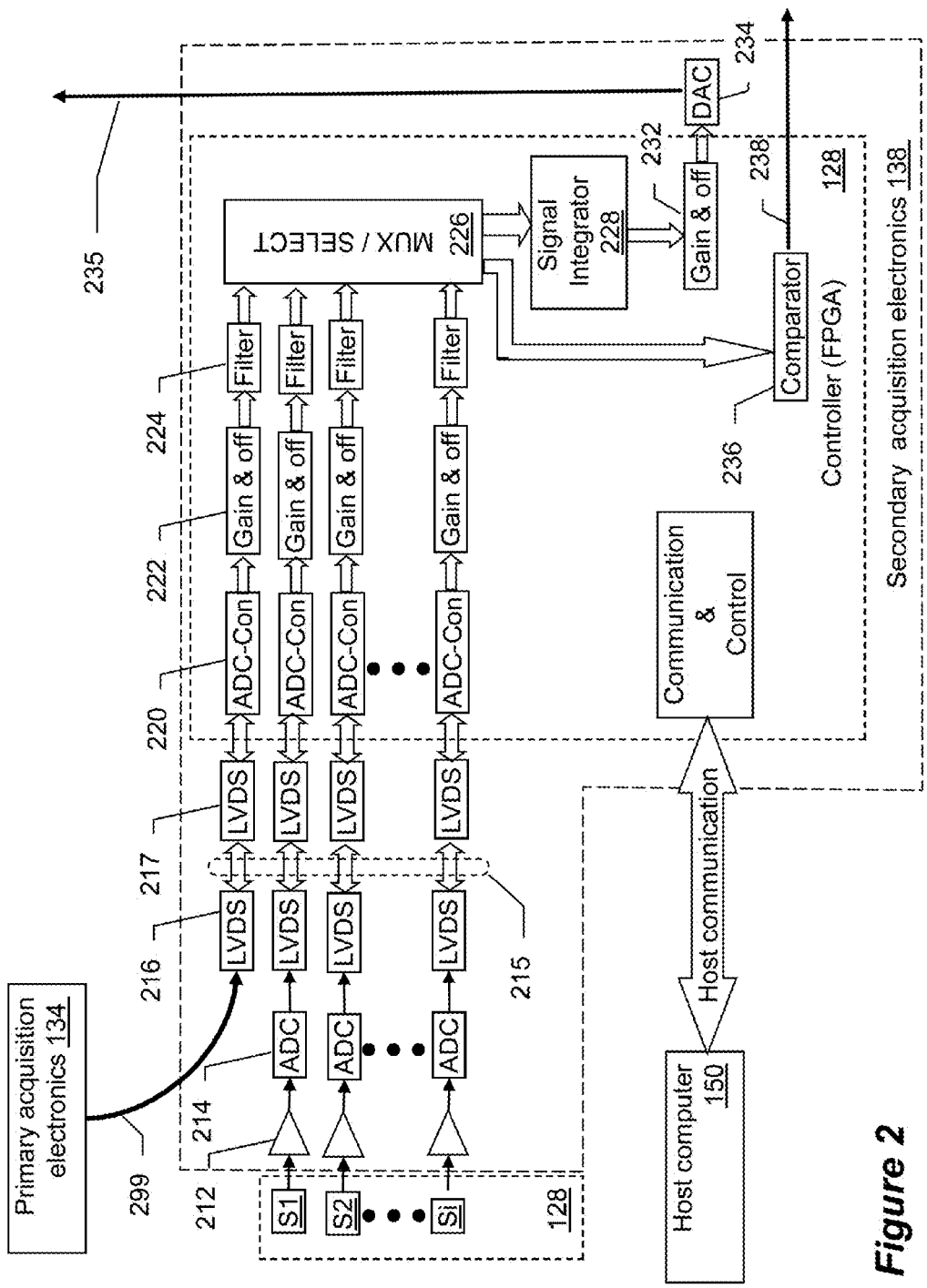
FIG. 2 schematically depicts an exemplary design of a block diagram of the electronic of the secondary radiation detector according to the current invention.

Some more details of the operation of the AEC function is given in FIG. 2, which explains how the AEC function may produces an "X-ray start" signal, which relates to the start of X-ray radiation on the FPD. Additionally and optionally a pre-set threshold is defined, which corresponds to the dark current of the light sensors. When no X-ray hits the FPD, the signal from the plurality of sensor corresponds to said dark current. Therefore, when tested against said threshed, typically half of the signals will be lower and half higher than said threshold. When X-ray starts, higher fraction of the signal will surpass the threshold value. The "X-ray start" signal may be used to start data acquisition by the primary acquisition electronics.

Autonomic initiation of data acquisition on detection of X-ray production allows autonomous operation of the FPD 120. Having this mode, a single FPD can serve a plurality of X-ray systems, without having to be hooked to any of them.

It should be noted that the marking in the figure of the electronic functions of the secondary acquisition electronics 138 and the AEC function is made for simplification of the block diagram, and the same board or chip may perform some functions related to both blocks.

In some optional embodiments, secondary acquisition electronics 138 performs the function of selecting, processing (such as averaging or performing weighted averaging) and integration of the signals that will be used for AEC. In some embodiments, secondary acquisition electronics 138 produces a single signal, to be compared with a threshold for terminating the X-ray exposure.

It is one optional advantage and aspect of the invention that a limited number of sensors 128 are used by AEC function, supplying representative sample of the radiation flux across the primary scintillator 122.

It is another optional advantage and aspect of the invention that sensors 128, and their connecting wires 158 are placed below the primary detector (the combination of primary scintillator 122 and primary imaging matrix 124), and, thus, detectors 128 may be placed anywhere across the field of view of the primary detector, without interfering with the image acquired by the primary detector.

It is yet another optional advantage and aspect of the invention that the AEC function is located within detector assembly 120. Thus, no external AEC unit is needed. Additionally, old X-ray units may be upgraded to include AEC by simply using the detector assembly of the current invention. Additionally, since detector assembly 120 comes with its AEC function, the parameters in AEC function may be adapted to the specifications of the primary detector in the assembly. Thus, replacing or changing to a different type of detector assembly requires no reprogramming of an external AEC unit or host 150. When the detector assembly is capable of initiating data acquisition on detection of X-ray as described above, replacing or exchanging the detector assembly does not require connecting it to a trigger line from the X-ray system, as it is self-triggering.

Signals of the primary detector, after it was acquired and digitized by primary acquisition electronics 124 needs correcting as discussed in the background section.

In an optional embodiment of the current invention, image correction unit 142 receives raw data from by primary acquisition electronics 124 and performs the required corrections before transmitting the corrected image to host computer 150. Some details of exemplary embodiment the image correction unit 142 are given in FIG. 4.

It is yet another optional advantage and aspect of the invention that the image correction unit 142 is located within detector assembly 120. Thus, no external image correction unit is needed, and no image correction program is needed within host 150. Additionally, old X-ray units may be upgraded to digital imaging simply using the detector assembly of the current invention. Additionally, since detector assembly 120 comes with its image correction unit 142, the parameters in image correction unit 142 may be adapted to the specifications of the primary detector in the assembly. Thus, replacing the detector assembly or changing to a different type of detector assembly requires no reprogramming of an external image correction unit or host 150.

FIG. 2 shows exemplary implementation of said secondary array circuitry according to an exemplary embodiment of the current invention.

As shown, signals from each sensor (for drawing clarity, three such sensors S1, S2, and Si of the array 128 are seen) is amplified by a preamp 212 and digitized by Analog to Digital Converter 214 (since all the channels are similar, only elements in the upper one are numbered). The plurality of digitized signals are transmitted through low-voltage differential signaling LVDS bus 215 using LVDS transceivers 216 and 217 to processing controller (for example, a Field Programmable Gate Array, or FPGA). An ADC-controller 220 controls the operation of the ADC 214, and the signal may optionally digitally compensated for offset and gain variation among the channels in gain and offset compensation 222. Optionally, noise is suppressed by a filter 224.

In the processing controller 128, Select/MUX 226 selects one or more of the signals for further processing and for outputting digital signals to the host computer 150 and/or to the X-ray generator 108. Said outputted digital signals are responsive to said processed sensor signals.

Optionally, additional inputs on the LVDS bus 215 are signals from the primary detector (for drawing clarity, only one such channel 299 is seen in this figure, but a plurality of channels may be used). Said signals can be either signals processed by the primary acquisition electronics 134, or raw data of the primary detector 124 which are processed by internal electronic within the secondary acquisition electronics 138. The FPGA controller 138 can select to use signals of the primary array only, of the secondary array only or a combination thereof.

An exemplary FPGA outputted signal is "X-ray start" signal, which relates to the start of X-ray radiation on the FPD. A pre-set threshold is defined, which corresponds to the dark current of the light sensors. When no X-ray hits the FPD, the signal from the plurality of sensor corresponds to said dark current. Therefore, when tested against said threshed, for example, in comparator 236, typically half of the signals will be lower and half higher than said threshold. However, when the X-ray starts, a higher fraction of the signals will surpass the threshold value. The more sensor signals are considered, the more accurate the threshold is set and more responsive is the system to actual starting of the X-ray radiation. Thus, said system can provide "X-ray start" signal 238 to the primary radiation detector. For example, such a signal may be used to start data acquisition by the primary acquisition electronics 124.

Another exemplary outputted signal is AEC signal 235 which is a ramp signal, linearly proportional to the dose hitting the FPD, for example, as attenuated by a average or specific locations of the patient. Said signal is an integral, digitally integrated by signal integrator 228. Integration may be applied to an average signal, or applied to an average over plurality of said sensor signals which are selected according to their position on the second sensor array. Optionally, the integrated signal further compensated for gain and offset 222. If needed, an analog AEC signal 235 is produced by Digital to Analog converter 234. Alternatively, a digital AEC is used for stopping HV generator 108.

Figure 3:
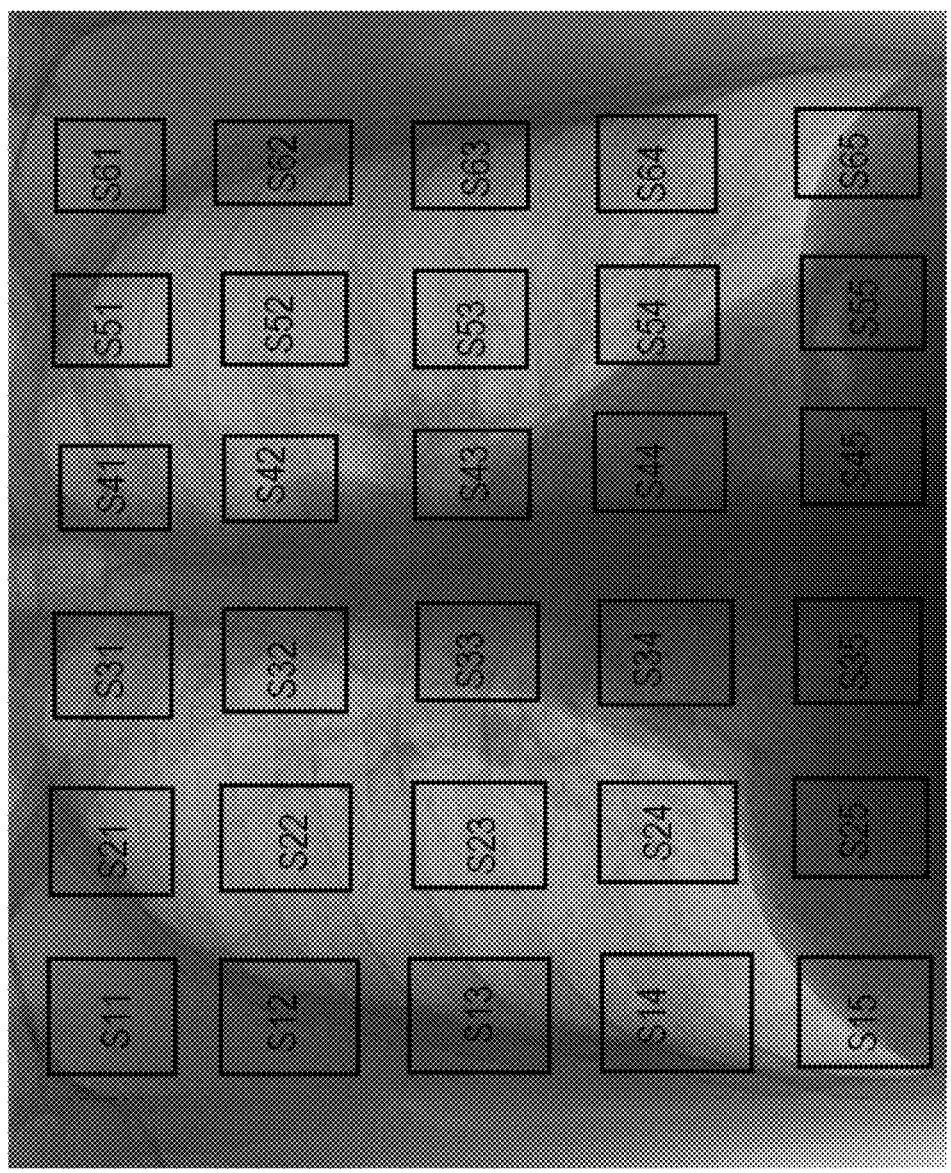
FIG. 3 schematically depicts an exemplary design of the secondary radiation detector, in geometry adopted for chest imaging according to the current invention.

FIG. 3 schematically depicts an exemplary design of the secondary radiation detector, in geometry adopted for chest imaging.

FIG. 3 schematically shows a transmission image of human chest on exemplary array of the secondary image sensors array. Each sensor outputs a signal which is proportional to the amount of radiation that hits the scintillator of the second array above it. Sensors that are located below the patient's lung has larger output signal, corresponding to the higher radiation dose on their adjacent scintillator area (although this signal is not necessarily the highest of the image, because sensor of the sides receive the complete impinging dose, without absorption). In the depicted embodiment sensor array 128 comprises of 6.times.5 array of 30 sensors, numbered S11, S12, . . . S15 in the first column to S61, S62, . . . S65 In the last. In an exemplary embodiment, controller 128, select/MUX 226 selects only these sensors of the second array with fast-increasing output, which are located behind the lungs (Sensors S22, S23, S24, S52, S53, and S64 can be considered as lung sensors). The average signal of these sensors is used as the ramp-shape "AEC" signal.

Another embodiment of AEC corresponds to signals of the primary detector. Signals of primary detector pixels can be selected as input for both the "X-ray start" and for AEC signals. For example, primary detector pixels can be selected according to their geometrical coordinates. In FIG. 3, squares numbers S22, S23, S24, S52, S53, and S64 are fully covered by the patient's lungs. Pixels of the primary detector that corresponds to these locations may be selected. In another embodiment, the primary detector has "trigger-pixels" whose signals are used by the secondary acquisition electronics 138 as input. A single trigger-pixel input can be used, or more than one trigger-pixel input can be used, or only these trigger-pixels that are located beneath said squares can be used.

Figure 4:
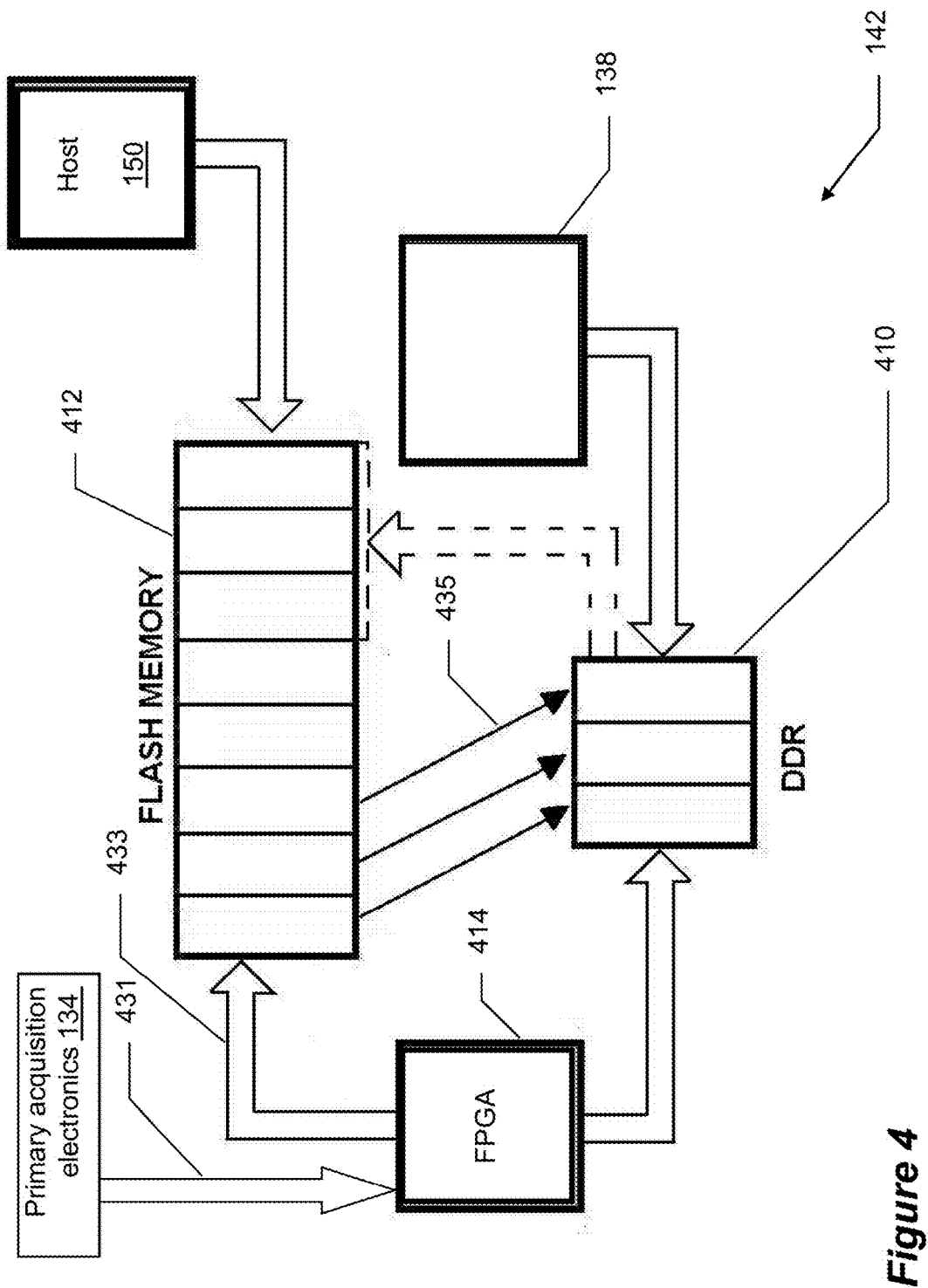
FIG. 4 schematically depicts an exemplary design of a block-diagram of the on-FPD calibration circuitry according to the current invention.

We now refer to FIG. 4, showing a block diagram of image correction unit 142 part of the primary electronic circuitry 134.

Image correction unit 142 circuitry comprises of Double-Data-Rate synchronous, dynamic random-access memory (DDR) 410 and of Flash memory unit 412. Further it comprises f Field programmable gate array (FPGA) 414 and the outputs of secondary electronics 138 described above.

This circuitry supports two modes of operation:
a calibration mode, and
a clinical measurement mode.

In calibration mode, three tables are created: offset table, gain table, and defect table. Offset and gain tables are evaluated in a similar way, where data of plurality of images (dark images for offset, and no-absorption X-ray illumination images for gain) are collected by the Primary acquisition electronics 134, transferred (431) to, and averaged by the FPGA 144. Said average images are representative matrixes. For the offset table, the representative matrix contains the value to be subtracted from each measured clinical value and it is sent (433) to the flash memory 412 for storage. For the gain table, the representative matrix has, for each pixel, a representative value that is proportional to the sensitivity of the pixel. Then, the FPGA computes the average of the representative matrix and computes the gain-correction table, which is the inverse of said representative matrix, multiplied by said average. Said gain-correction matrix is also sent (433) to the Flash memory 412 for storage.

Defective pixels are detected by a specialized algorithm that comprises testing the various physics characteristics of the imaging pixels: dark signal, sensitivity, and linearity and listing the pixels with exceptional characteristics exceeding pre-set thresholds. The FPGA uses said dark and flat scans for determining those pixels with exceptional dark and gain values and listing them as defective pixels. Again, the list is transferred (433) to, and stored in the Flash memory 412.

Calibration process may be repeated and the result updated as needed.

In clinical mode, the three tables, offset, gain, and defects are fetched (435) from the Flash memory 412 and stored in the DDR 410. The gain table is skewed to compensate for radiation distribution, according to the distance between the X-ray source and the FPD. Clinical data is collected by the Primary radiation detector, digitized by the Primary acquisition electronics 134 and is sent to the DDR 410. The FPGA 414 subtracts the corresponding data of the offset table and multiplies by the data of the skewed gain table. Then, the defective pixels are substituted by their respective neighbors, in a way that the edge image is not affected as disclosed in FIGS. 5A and 5B.

Figure 5A:
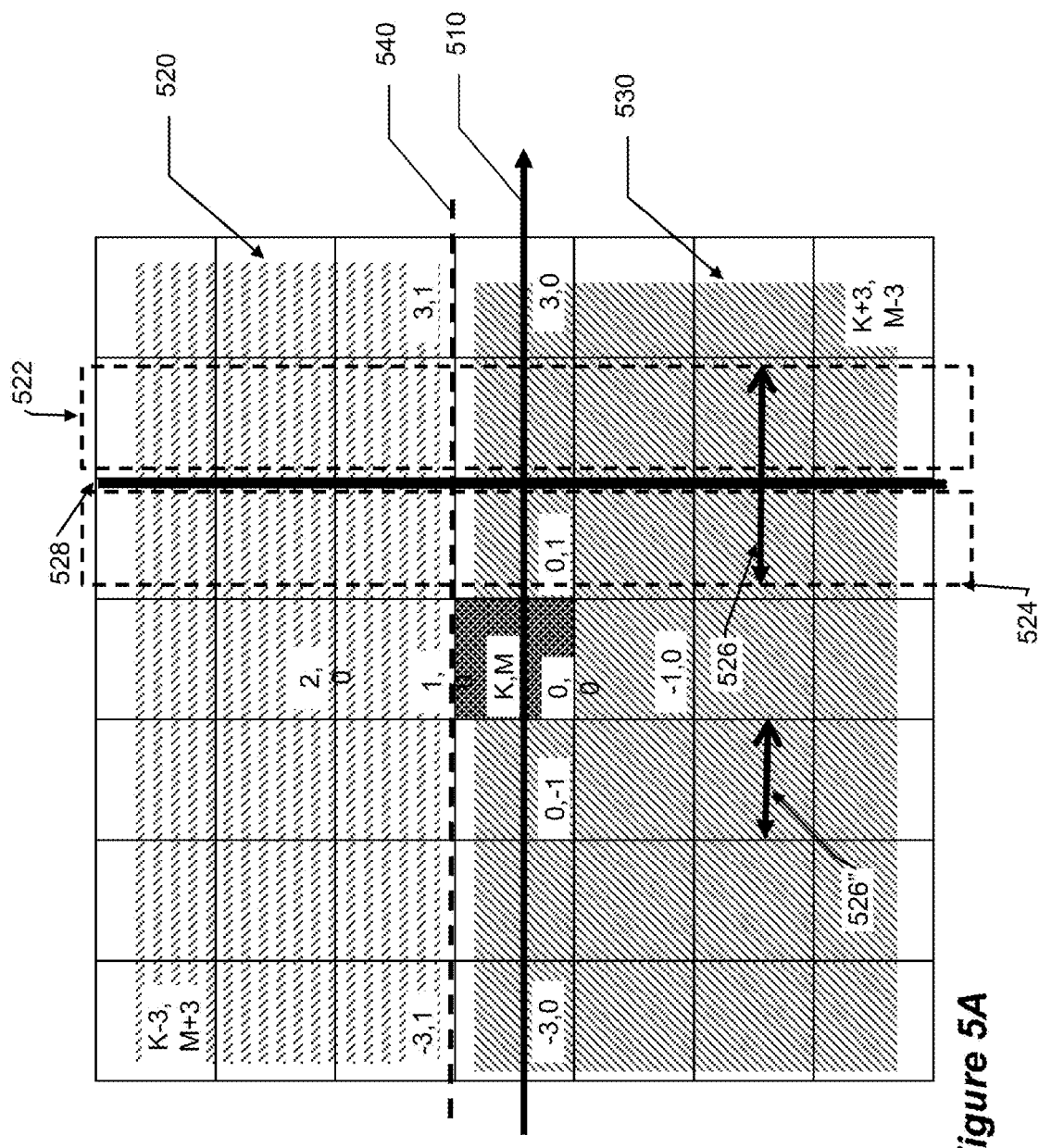
FIG. 5A schematically depicts an exemplary method of correcting defective pixels in an edge-conformal method according to the current invention.
Figure 5B:
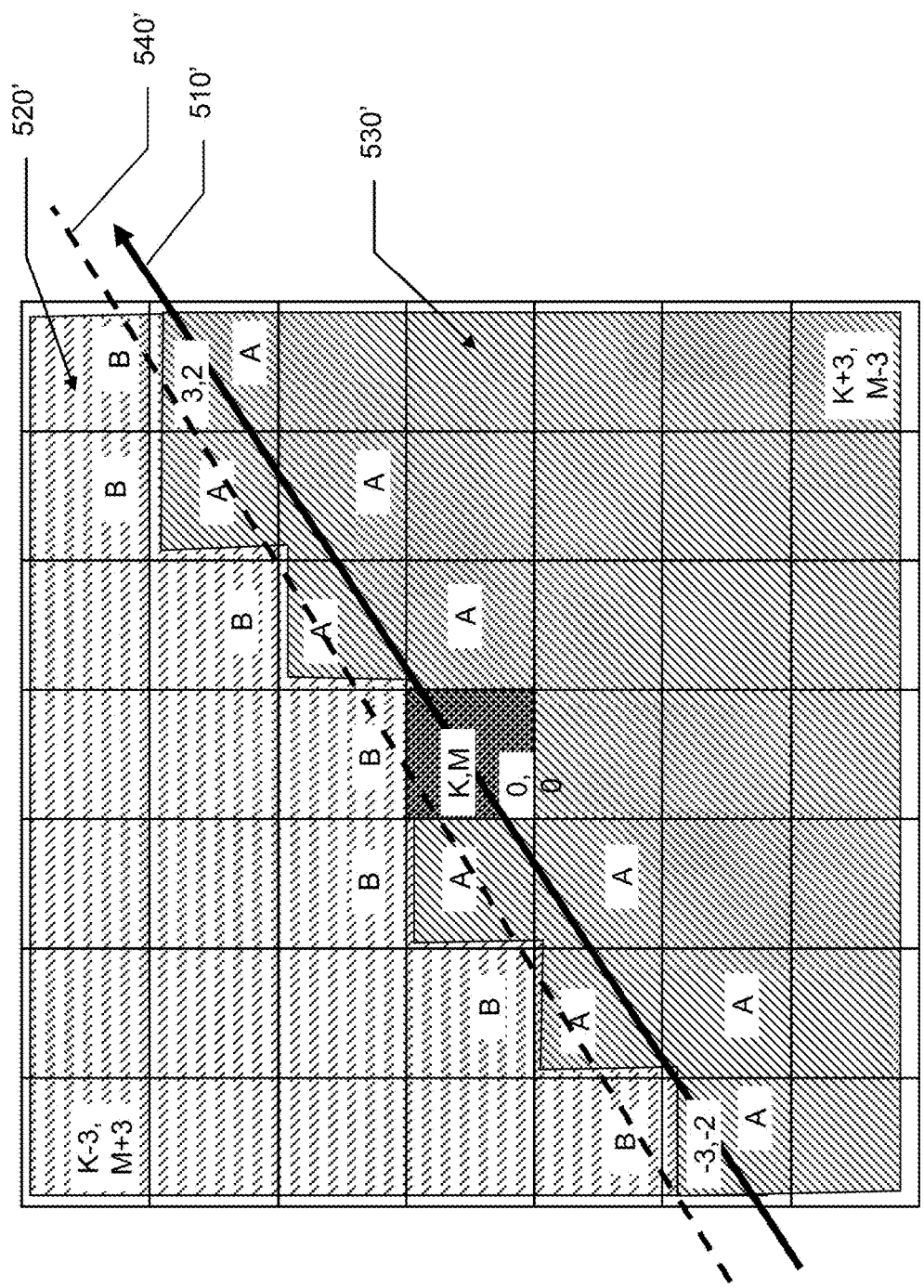
FIG. 5B schematically depicts another example of the method of correcting defective pixels in an edge-conformal method according to the current invention.

FIGS. 5A and 5B describes the method in which an isolated defect is corrected in edge-conformal way.

It should be noted that the primary imaging matrix 124 comprises a very large number of pixels, and thus, few may be damaged during manufacturing or become defective during work. In many cases, the defective pixel is isolated, that is there are no other defective pixels near it.

FIGS. 5A and 5B depict a small section of 7×7 pixels, centered around a defective pixel having coordinates $\{K,M\}$ in the 2D array of pixels. The relative coordinates of nearby pixels are given by the distance from the center, that is in the range $\{-3,-3\}$ to $\{3,3\}$ with the corresponding absolute coordinates $\{K+3, M+3\}$, etc.

In one exemplary embodiment, the value of the damaged pixel is assigned by a weight average of the some of the surrounding pixels. For example a matrix A[i,j] may be constructed such that j=$\{-3,3\}$, k=$\{-3,3\}$, A$\{0,0\}$=0, and v$\{0,0\}$=Sum[v$\{I,j\}$*A$\{i,j\}$]. Preferably, matrix A is symmetric, positive, and value preserving such that Sum[A$\{i,j\}$]=1. It should be noticed that larger or smaller than 7×7 matrix may be used.

It is yet another object of the current invention to assign to a defective pixel a value that does not degrade the sharpness of the image. The weighted averaging method of assigning a value to a defective pixel is equivalent to a "low-pass-filtering" performs on that defective pixel. As such, it has an "image smoothing" effect. X-ray images include sharp edges such as bone boundaries and other boundaries between organs. When viewed locally (that is on a small area of neighboring pixels), such boundaries are seen nearly as a boundary line between two domains, in which the pixels are having a similar values.

In this exemplary embodiment, a 7×7 sub-matrix is considered with the defective pixel at the center. A plurality of major directions lines is defined, and the directional-derivate is evaluated for each of the lines. A line directional-derivate is the difference between the average value of pixels on the direction line ("direction pixels") and the average of pixels nearest to said direction pixels, on one side of the line. The value of the defective pixel is replaced by the average value of the directional pixels on the direction line with the maximal absolute value of the directional-derivative.

FIG. 5A schematically depicts an example of using the method of correcting defective pixels in an edge-conformal method according to the current invention.

In this figure, the boundary between the domains 520 and 530 runs approximately along the dashed line 540. Thus, the directional line with maximal line-derivative is designated as arrow 510 which connects pixels $\{-3,0\}$ and $\{3,0\}$.

The line-derivative in this case is the sum of the values of pixels $\{-3,0\}$ to $\{3,0\}$ divided by six (as pixel $\{0,0\}$ is defective) minus the sum of pixels $\{-3,1\}$ to $\{3,1\}$ divided by seven. Pixel $\{0,0\}$ is assigned with the value of the sum of the values of pixels $\{-3,0\}$ to $\{3,0\}$ divided by six. It is preferable that the processing board interpolates, in real-time, the values of the peripheral pixels into a whole number of interpolated values, the number is equal to the whole-number width.

It is also preferably that the processing board interpolates, in real-time, the values of the peripheral pixels into a whole number of interpolated value. The number is equal to the whole-number width without crossing the detected image edges.

Peripheral pixels are defined as any pixel that resides between two buttable CMOS wafers. In FIG. 5A, dashed right hand side rectangular 522 and left hand side rectangular 524 that indicates the two buttable CMOS wafers pixel lines clarify the terms total width of the two peripheral pixel lines indicated by arrow 526 and the gap or spacing between them 528, as well as the term pixel pitch indicated by arrow 526" that are shown and indicated in the figure.

FIG. 5B schematically depicts another example of using the method of correcting defective pixels in an edge-conformal method according to the current invention.

In this figure, the boundary between the domains 520' and 530' runs approximately along the dashed line 540'. Thus, the directional line with maximal line-derivative is designated as arrow 510' which connects pixels {-3,-2} and {3,2}.

The line-derivative in this case is the average of the values of pixels marked with "A" minus the average value of pixels marked with "B". Pixel {0,0} is assigned with the average of the values of pixels marked with "A".

In cases where other pixels of the 7×7 pixels are defective the same method is used without including the defective pixels and optionally their respective nearest-neighbors in the calculation.

It should be noted that matrix with dimensions other than 7×7 may be used within the general aspect of the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

As used herein, the term "computer", processor, or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods.

The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A radiation detection system comprising:
   a scintillator capable of converting the radiation to visible light;
   at least two buttable CMOS wafers;
   an adjacent acquisition board, for acquiring pixel values; and
   at least one processing board capable of image edge detection, wherein the butt of each pair of adjacent CMOS wafers is made such that the total width of two peripheral pixel lines and the spacing between them sums to a whole number of pixel pitch, N, and
   wherein said processing board:
   a) subtracts the corresponding data of an offset table from pixel values;

b) multiplies the resulted value by the data of a skewed gain table;
c) substitutes the values of at least one defective pixel by a value derived from values of pixels in a zone around said at least one defective pixel, in a way that the image edge is not affected; and
d) produces N virtual data lines with information derived from the two peripheral lines and the lines adjacent to them, wherein said data is composed such that edges presented in the peripheral and adjacent lines are conserved in the additional N lines.

2. The radiation detection system as in claim 1, wherein the total width of the two peripheral pixel lines and the spacing between them sums to a single pixel pitch.

3. The radiation detection system as in claim 1, wherein the total width of the two peripheral pixel lines and the spacing between them sums to double the pixel pitch.

4. The radiation detection system as in claim 1, wherein substituting values of a defective pixel with a value derived from values of pixels in a zone around said defective pixel, in a way that the image edge is not affected comprises interpolating values of pixels located on one side of the detected image edge passing through said defected pixel.

* * * * *